United States Patent [19]
Shvartz et al.

[11] Patent Number: 5,158,093
[45] Date of Patent: Oct. 27, 1992

[54] UNIVERSAL FITNESS TESTING SYSTEM

[76] Inventors: Esar Shvartz, 3530 Marna Ave., Long Beach, Calif. 90808; Robert C. Reibold, 5849 Candlewood St., Lakewood, Calif. 90713

[21] Appl. No.: 613,856
[22] PCT Filed: Apr. 24, 1989
[86] PCT No.: PCT/US89/01735
  § 371 Date: Jan. 23, 1991
  § 102(e) Date: Jan. 23, 1991
[51] Int. Cl.$^5$ ............................................. A61B 5/02
[52] U.S. Cl. ................................. 128/707; 128/668; 128/25 R; 128/671; 128/670; 128/680
[58] Field of Search ............. 128/700, 702, 725, 25 R, 128/670, 706, 671, 668, 680; 272/73; 364/413.02, 413.03, 413.04

[56] References Cited

U.S. PATENT DOCUMENTS

| | | | |
|---|---|---|---|
| 4,807,639 | 2/1989 | Shimizu et al. | 128/706 |
| 4,860,763 | 8/1989 | Schminke | 128/707 |
| 4,976,424 | 12/1990 | Sargeant et al. | 128/707 |
| 4,998,725 | 3/1991 | Watterson et al. | 128/25 R |

Primary Examiner—Kyle L. Howell
Assistant Examiner—George Manuel
Attorney, Agent, or Firm—Albert O. Cota

[57] ABSTRACT

A universal fitness testing system (10) that allows individuals to determine their aerobic fitness in 30-seconds. The system (10) functions with two inputs: the first is a set of pulse-rate digital signals corresponding to the pulsations of the individual's cardiovascular system. These signals are derived by performing a 30-second test that ultimately produces a uniform work load (14). The second input is a set of user-specific digital signals corresponding to the individual's age, body weight and sex that are manually inputted and processed by an electronics keyboard (36). The two signals are processed and conditioned by an electronics unit (18) before being applied to a microcomputer (12). The microcomputer with its operational program processes the signals to derive the individual's equilibrium heart rate (12b) that is then corrected by sex and age standards (12c) and $V_{O_2}$ max standards (12d), (12e) to produce fitness scores and categories. The corrected equilibrium heart rate also produces % $V_{O_2}$ max (12h) from where exercise capacity, fitness age and hiking fitness are produced.

9 Claims, 5 Drawing Sheets

A = PULSE RATE DIGITAL SIGNALS
B = USER-SPECIFIC DIGITAL SIGNALS

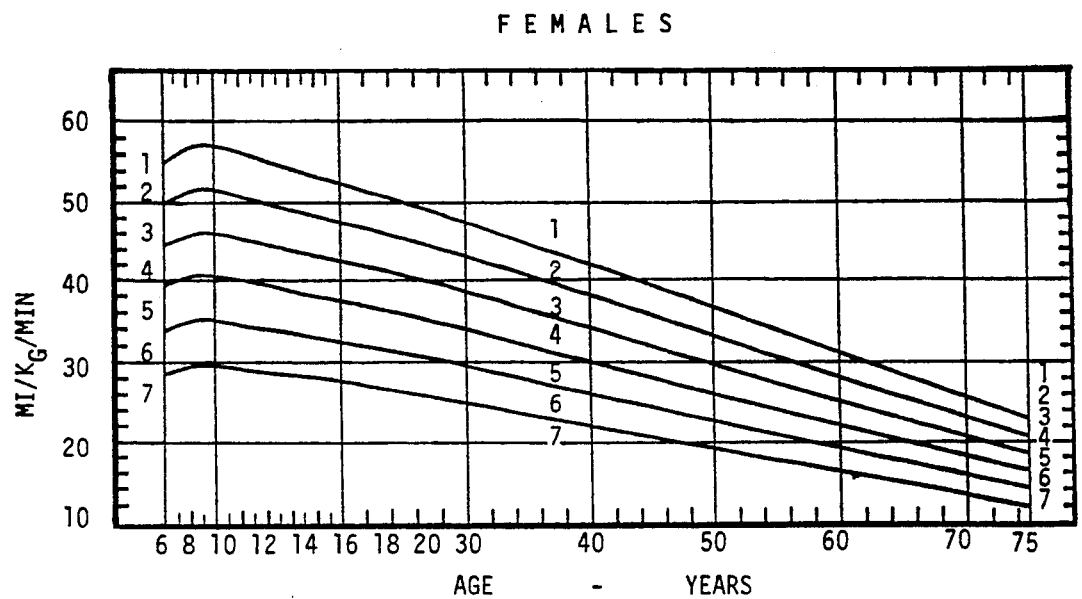
FIG. 3 A
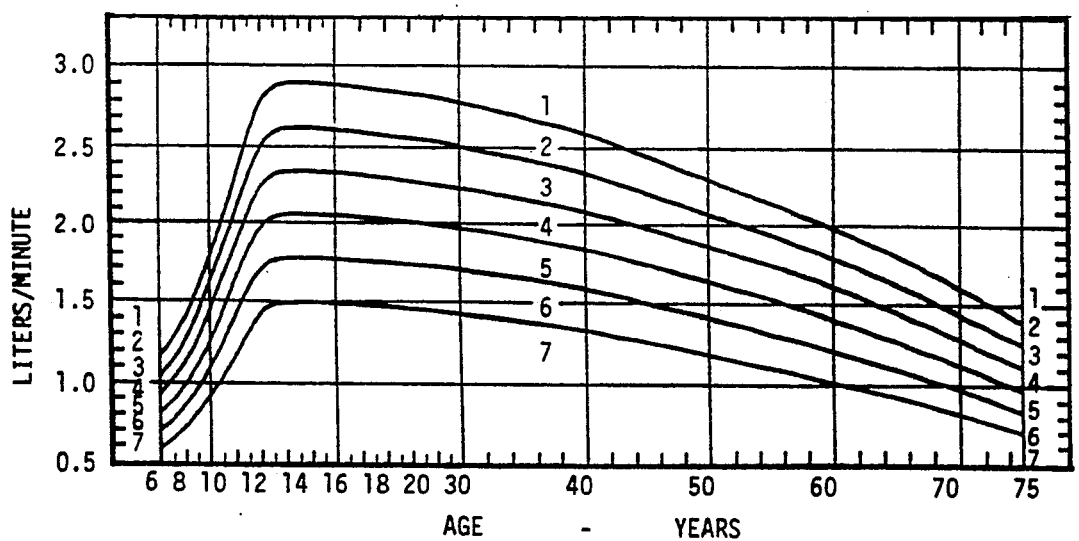
FIG. 3 B

UNIVERSAL FITNESS TESTING SYSTEM INPUTS, OUTPUTS AND EXAMPLES

| INPUTS | | EXAMPLE | OUTPUTS | EXAMPLES |
|---|---|---|---|---|
| PRIMARY | | | | |
| AGE | | 40 | $V_{O_2}$ MAX | |
| SEX | | MALE | L/min | 3.2 |
| WEIGHT kg | | 84 | mL/kg·min | 38 |
| lbs | | 185 | | |
| HEART RATE | | | FITNESS SCORES | |
| | | | L/min | 70 |
| | | | mL/kg·min | 70 |
| SECONDARY | | | | |
| STEPPING RATE | | 16 | | |
| ALTITUDE | | | FITNESS CATEGORIES | |
| TESTED | ft | 0 | L/min | Average |
| | M | 0 | mL/kg·min | Average |
| PERFORMED | ft | 6,000 | | |
| | M | 1,820 | FITNESS AGE | 40 |
| HEART | | | | |
| AIR TEMP | | | EXERCISE CAPACITY | |
| TESTED | °C | 23 | RATE | 5.5 miles |
| | °F | 75 | | 8.8 km/hr |
| PERFORMED | °C | 40 | DISTANCE | 5.3 miles |
| | °F | 104 | | 8.5 km |
| HUMIDITY | | | | |
| TESTED | | Average | HIKING FITNESS | 2 miles/hr |
| PERFORMED | | Humid | | 3.2 km/hr |
| HIKING | | | INDUSTRIAL FITNESS | 0.97 l/min |
| TOTAL HIKE Miles | | 12 | | |
| DISTANCE km | | 19.2 | | |
| ALTITUDE gain ft | | 3,000 | | |
| M | | 912 | | |
| ALTITUDE LOSS | | | | |
| ft/miles walked | | 3,000/6 | | |
| m/km walked | | 912/9.6 | | |
| LOAD CARRIED kg | | 10 | | |
| lbs | | 22 | | |
| TERRAIN FACTOR | | 1.5 | | | ft = feet; M = meters; km = kilometers; kg = kilograms

FIG. 5

UNIVERSAL FITNESS TESTING SYSTEM

TECHNICAL FIELD

The invention pertains to the general field of aerobic fitness testing and more particularly to a universal fitness testing system that provides aerobic fitness information after a 30-second exercise test which utilizes heart rate reactions.

BACKGROUND ART

Aerobic fitness, the ability to sustain endurance type work for prolonged periods, is the major factor in physical fitness. This capacity is usually expressed in walking, running, swimming and related activities and is determined by the measurement of maximum $O_2$ uptake ($V_{O_2}$ max). Two aspects of $V_{O_2}$ max are important: absolute $V_{O_2}$ max, the maximum amount of oxygen that one is able to consume during the performance of maximal work, expressed in liters/minute of oxygen (l/min); and relative $V_{O_2}$ max, which is the absolute $V_{O_2}$ max divided by body weight and expressed in milliliters of oxygen per body weight per minute (ml/kg·min). Absolute $V_{O_2}$ max represents fitness where body weight is not a factor in performance such as during swimming, lifting, cycling, and the like. Relative $V_{O_2}$ max represents fitness where body weight is lifted during performance such as in walking, running, hiking and the like. There is a large body of knowledge showing that $V_{O_2}$ max is positively related to good health and longevity. A direct determination of $V_{O_2}$ max, however, requires an expensive laboratory setting and is beyond the reach of most persons.

During the past half century, several attempts have been made to predict endurance fitness in adults. These early tests were based on heart rates that were manually recorded during recovery from a standard exercise, which were very inaccurate and did not include any standards. Later tests considered work load and heart rate for the prediction of $V_{O_2}$ max, and this has remained the basis for all such tests. The physiological basis for the latter tests is simple: mechanical work load is proportional to oxygen uptake (energy expenditure), with little variability. Mechanical work load can easily be determined when performing on a bicycle ergometer (it equals the resistance to cycling); in an uphill walk or run on a treadmill (height to which body weight is lifted), or in stepping where work load is determined as in an uphill walk. Thus, oxygen uptake can accurately be determined by the performance of the above types of work. It is also known that heart rate increases linearly with an increase in oxygen uptake. If heart rate is recorded during at least two different work loads, and the former is plotted against the latter, a best fit straight line is drawn through these points and an extrapolation is made to the assumed maximal heart rate of the individual, which is age related. This point corresponds to the $V_{O_2}$ max of the individual. Thus, low heart rates recorded during the submaximal loads indicate a high $V_{O_2}$ max, while high heart rates indicate a low $V_{O_2}$ max.

The most famous test for $V_{O_2}$ max prediction was presented by Åstrand I (aerobic work capacity in men and women with special reference to age. *Acta Physiol. Scan.* 1960; 49, Supp. 196). The test consisted of exercising at one load on a bicycle ergometer and then measuring the heart rate after 5 or 6 minutes. Correlation tests conducted on a large number of men and women showed good correspondence with $V_{O_2}$ max determined directly. The disadvantages of this test are similar to those of other tests of the same category. It is necessary to perform at least five minutes of strenuous work to determine equilibrium heart rate since it takes at least five minutes for the heart rate to level off at a particular submaximal work load. This method of determining the equilibrium heart rate has several other disadvantages: it is strenuous for most people; the presence of a specialized stationary bicycle ergometer is necessary; the fitness scores are based on only a Swedish population that may not apply to other populations; and the test is applicable to adults only.

Other tests for the prediction of $V_{O_2}$ max, where more than one work load is performed, are more accurate than the Åstrand test. Computerized systems are now available, using bicycle or treadmill ergometers. The operator exercises at three different work loads, and the computerized system calculates the work loads, monitors the heart rates, plots the latter against the former, and extrapolates to the load corresponding to the age-dependent assumed heart rate. Oxygen uptake at that load is the $V_{O_2}$ max of the individual. An example of such a system is described in U.S. Pat. No. 4,408,613 issued to Relyea, R. D. The disadvantages of the computerized $V_{O_2}$ max prediction systems are: at least ten minutes of strenuous exercise are required. Adequate rest is required between the exercise periods for accurate heart rate determination, availability of expensive and stationary equipment, lack of universally accepted $V_{O_2}$ max standards and the tests are applicable only to adults.

A major additional disadvantage of all the $V_{O_2}$ max prediction tests discussed above is that they are designed for a general $V_{O_2}$ max status prediction, for instance, their purpose is to determine $V_{O_2}$ max of an individual at a particular time period in his/her life. It is not possible to perform multiple determinations. The reason for this is that all the above tests require the individual being tested to go to a specific location, wear gym clothes, and perform strenuous exercise, which is inconvenient and very difficult to do for most people, even if expense is not considered.

The $V_{O_2}$ max status determination is important for general health information, to monitor progress achieved during a training program, or for athletic screening. Existing tests can, at best, inform users about their aerobic capacity on each given day. But even for this purpose, this information is largely theoretical if the results are to be used to predict performance capabilities on that day, since taking any of these tests induces fatigue. Thus, a very important health/fitness related test has not been available: a test allowing a quick estimation of aerobic capacity in a similar manner to the determination of body weight or blood pressure. It should be noted that the minimum frequency in which the determination of the latter functions are of interest (except in emergency conditions) is on a daily basis, while hourly, or a multi-daily fitness determination could be of great interest to millions of people engaged in work, exercise and sports, athletic competition, recreational pursuits and military activities.

A search of the prior art did not disclose any patents that read directly on the claims of the instant invention however, the following U.S. patents were considered related:

| U.S. PAT. NO. | INVENTOR | ISSUED |
| --- | --- | --- |
| 4,463,764 | Anderson, et al | 7 August 1984 |
| 4,450,527 | Sramek | 22 May 1984 |
| 4,408,613 | Relyea | 11 October 1983 |
| 3,675,640 | Gatts | 11 July 1972 |

The Anderson et al patent discloses a cardiopulmonary exercise system for real time breath-by-breath acquisition, analysis, display and printing of an individual's physiologic parameters. The system includes a microprocessor based waveform analyzer that receives inputs from a $CO_2$ analyzer, an EGG monitor, an $O_2$ analyzer and a pneumotachograph. The waveform analyzer provides output data to a host CPU to which a CRT display or hard-copy printer may be connected to provide the medical data for assessment of an individual's heart and lungs.

The Sramek patent discloses a noninvasive continuous cardiac output monitor and a method using electrical bioimpedance measurements to monitor parameters associated with blood flow in a segment of body tissue. The invention eliminates the effect of respiration from the thoracic impedance as a function of time to provide a continuous signal indicative of pulstile thoracic impedance changes. The produced impedance signal is processed to produce signals indicative of the ventricular ejection time and the maximum rate of change of pulsatile thoracic impedance. This change is used in a microprocessor to calculate the volume of blood pumped per stroke according to an improved systolic upstroke equation.

The Relyea patent discloses an interactive exercise device that utilizes an exercise bicycle wherein wheel speed and force are monitored. An electromagnetic brake is adjusted by a control apparatus to relate the measured force to the required force. The electromagnetic brake controls the drag to implement a selected exercise program that paces the user through a specified load for a specified interval. The work load can be varied in any manner to achieve a desired exercise program. The program is recorded on a video cassette. On playback, the cassette provides the video for the monitor that is viewed by the user.

The Gatts patent discloses an apparatus for dynamic health testing, evaluation and treatment comprising the recordation of test data from large numbers of individuals to establish dynamic physical performance norms for patients of many varied types. Historical data is taken from a patient which, in conjunction with a physical examination, is used to establish a specific theoretical dynamic physical performance norm for that particular patient and the recommended loading for the dynamic health testing machine. The patient is placed on the exercise machine which is under a programmed load based upon the basic data and numerous parameters of the patient's state of health are monitored under dynamic conditions. The monitored information is continuously fed back to correct the programmed load to protect the patient against overstress. The patient's performance is then compared with his own theoretical norm and treatment is recommended consistent with the patient's age and health which would lead toward the achievement of the dynamic physical performance norm.

DISCLOSURE OF THE INVENTION

The universal fitness testing system allows a near instantaneous (30-second) determination of aerobic fitness and other related fitness information. The test methodology used for the system is based on over 20 years of research conducted by the inventor. In numerous studies, dealing with a variety of topics, where continuous measurements of heart rate were recorded, it was noticed that the heart rate during the first minute of exercise was a highly reliable measurement. This measurement indicated a similar rate of change upon repeated recordings conducted on different days.

In over 50 male and female subjects of different ages, it was shown that the rate of change in cardiac frequency during the first 30-seconds of exercise was a highly reliable measurement. The test and retest correlation coefficient was $r=0.95$. These tests were conducted when the subjects had not exercised for several hours prior to the test, however, they were not asked to rest before the testing. Further experiments conducted in 25 male and female subjects, 6 to 78 years of age, also indicated that the rate of increase in cardiac frequency during the first 30-seconds of exercise correlated highly with the equilibrium heart rate, in this case the correlation coefficient was $r=0.923$. In the above tests, a standard exercise load test was established that preferably consisted of stepping up and down a 23.5 cm (9.25 inches) high stool, nine times for 30-seconds (18 steps/minute). This test equals a uniform work load of 0.69 watts/kg body weight that forms the basis for the universal fitness testing system.

Subsequent experiments performed on 17 male and female subjects ranging in ages from 6 to 55 years, further indicated that if the testing was performed after a mild exercise, such as after a minor walk or after climbing two or three flights of stairs, there were no differences in the predicted equilibrium heart rate when compared with taking the test after a long rest.

When the tests were performed following hard/prolonged exercise, they resulted in higher predicted equilibrium heart rates, which truly represented fatigue conditions. Taking the test after a brief exhaustive exercise resulted in a decrease in the rate of cardiac frequency and in corresponding predicted equilibrium heart rates which represented recovery from fatigued conditions. This means that aerobic fitness is decreased immediately following brief, strenuous exercise but it returns to a normal level if the test is taken following an appropriate recovery period. Thus, the universal fitness testing system can quickly predict the aerobic capacity of an individual in fatigued and non-fatigued conditions. For the first time, it is now possible to predict how far one can go following an exercise of different intensities and durations. But the primary novelty of the invention system is that for the first time, it is possible to have an almost instantaneous information about one's aerobic capacity.

The aerobic fitness predictions described above are based on equilibrium heart rate, corrected for age and body weight. Males and females are considered separately. In the 25 subjects mentioned earlier, $Vo_2max$ (directly determined) had a correlated coefficient of $r=0.91$ with $Vo_2$ max predicted from equilibrium heart rate (the latter corrected for age and weight). A similar correlation ($r=0.908$) was obtained between the rate of change in the heart beats during the universal fitness testing and the directly measured $Vo_2$ max in the above 25 subjects.

An assessment of an individual's $Vo_2$ max requires a comparison with a particular age and sex group. Therefore, $Vo_2$ max standards are needed. Prior to the instant invention, such standards were not available, except for the limited Swedish standards discussed earlier. Existing systems for $Vo_2$ max prediction and all other $Vo_2$ max evaluation efforts designed to rate individuals according to age and sex, have used various standards without a community agreement about what these standards should be. Consequently, wrong interpretations of $Vo_2$ max have often occurred. Additionally, no $Vo_2$ max standards have existed for children and adolescents.

The universal fitness testing system is based on universal $Vo_2$ max standards that were developed by the applicant through an extensive literature review and testing of 85 male and female subjects of different ages. These standards, which for the first time included data on children and adolescents were recently submitted for publication and are included as FIGS. 4 and 5. The fitness scores and categories obtained by the universal fitness testing are based on these standards. The present standards apply to most people in the industrial world. Standards for potential users of the universal fitness testing system belonging to other populations can be extrapolated.

The present standards allow a determination of the "fitness age" of an individual, which is the chronological age corresponding to a particular $Vo_2$ max. For example, the $Vo_2$ max of a 50 year old male is 2.7 liters/minute. In this case, his "fitness age" corresponds to his chronological age, since 2.7 liters/minute is the average $Vo_2$ max for this age and sex group. Thus, in this case "fitness age" = 50. If his $Vo_2$ max was 3.2 liters/minute, "fitness age" would have been 30, because this is the average $Vo_2$ max for 30 year old males. If it was 2.3 liters/minute, "fitness age" would have been 62.

In addition to $Vo_2$ max scores, categories and "fitness age", the universal fitness system allows, for the first time, the prediction of: exercise capacity, hiking fitness and estimated decrements in aerobic capacity resulting from expected performance in heat and/or altitude. Exercise capacity is in terms of the maximum rate of level walking/running that can be maintained aerobically and also in terms of the maximum distance that one can walk/run while approximately maintaining the above rate of work. In most people, this corresponds to the maximum rate of work that can be maintained, without rest for approximately one hour. However, very fit people, such as marathon runners, can run long distances at a high rate of work that can be maintained for two hours or more. On the other hand, very unfit and/or older persons cannot maintain even a low level walking rate for 30 minutes. Although no known aerobic test existed which provided the above exercise capacity predictions, ample evidence existed in the literature (including data of the present applicant) to allow estimation of level walking/running capability in adults. This capacity in adults is simply a function of relative $Vo_2$ max since it involves the lifting of body weight. Thus, a relatively light person with a high absolute $Vo_2$ max can walk/run faster than a heavy person with a low absolute $Vo_2$ max.

The above prediction capability did not exist with respect to children and adolescents. Empirical and experimental data have shown that walking/running fitness in children is not related to absolute or relative $Vo_2$ max because of the confounding influences of growth, maturation and low body weight. In the universal fitness testing system, a new concept, based on a percentage of $Vo_2$ maximum (% $Vo_2$ max), is used for the above prediction. This is the energy expenditure used during the preferred standard test of stepping nine times on a 23.5 cm high stool for 30-seconds and is expressed as a percentage of the absolute $Vo_2$ max. Data in the literature and recent data of the applicant have shown that % $Vo_2$ max can be used for the prediction of exercise capacity, independent of age.

For example, % $Vo_2$ max of an average seven year old boy is 50, which is equal to that of an average 47 year old man. Experience has also shown that the above individuals have similar walking/running capabilities. If absolute $Vo_2$ max is used for the prediction of exercise capacity, this capacity would be much lower in the average fit seven year old, than in the average fit 47 year old. If relative $Vo_2$ max is used for the same purpose, a much higher exercise capacity would be predicted in the seven year old, compared with the 47 year old, which would also be wrong. Thus, % $Vo_2$ max can be used to predict exercise capacity regardless of age or sex. Fit people with low % $Vo_2$ max have a high exercise capacity. Unfit people with a high % $Vo_2$ max have a low exercise capacity.

The prediction of aerobic capacity in heat, at altitude and during hiking under varying conditions did not exist in any known prediction system. In almost all cases, the above capabilities would indicate decrements compared with level walking/running at sea level under comfortable thermal conditions.

The prediction of exercise capacity in heat is based mostly on the applicants research on heat stress and exercise capacity in heat conducted during the past 20 years. Hiking fitness is based on the applicants own data, collected on himself and fellow hikers during several years of hiking in the trails and mountains of Southern California. Fitness at altitude is based on ample data available in the literature on decrements of $Vo_2$ max at different altitudes.

The universal fitness testing system allows performance predictions to be made at any altitude ranging from sea level to 16,000 feet (4,877 meters). Combinations of the above are also possible, such as prediction of exercise capacity in heat and altitude, hiking fitness and heat and/or altitude.

Hiking fitness is defined in terms of rate of walking (or running in very fit individuals) that can be maintained during a typical day's hike of approximately eight hours. Corrections for load carried, terrain (asphalt, sand, snow and the like) altitude gain, and altitude loss are also possible in addition to heat and/or altitude.

The universal fitness testing system has an additional capability of predicting "industrial fitness" which is defined as the safe energy expenditure that one can maintain in manual jobs without fatigue. This is simply one-third of absolute $V_2$ max. This information is especially important for job screening and job evaluation. Industrial fitness can also be predicted in heat and/or altitude.

These and other objects and advantages of the present invention will become apparent from the subsequent detailed description of the preferred embodiment and the claims taken in conjunction with the accompanying drawings.

BRIEF DESCRIPTION OF THE DRAWINGS

FIG. 3A, 3B is a diagram of the aerobic fitness ($V_{O_2}$ max) standards by sex and age for females.

FIG. 5 is a table listing the inputs and outputs with examples.

BEST MODE FOR CARRYING OUT THE INVENTION

Figure 1:
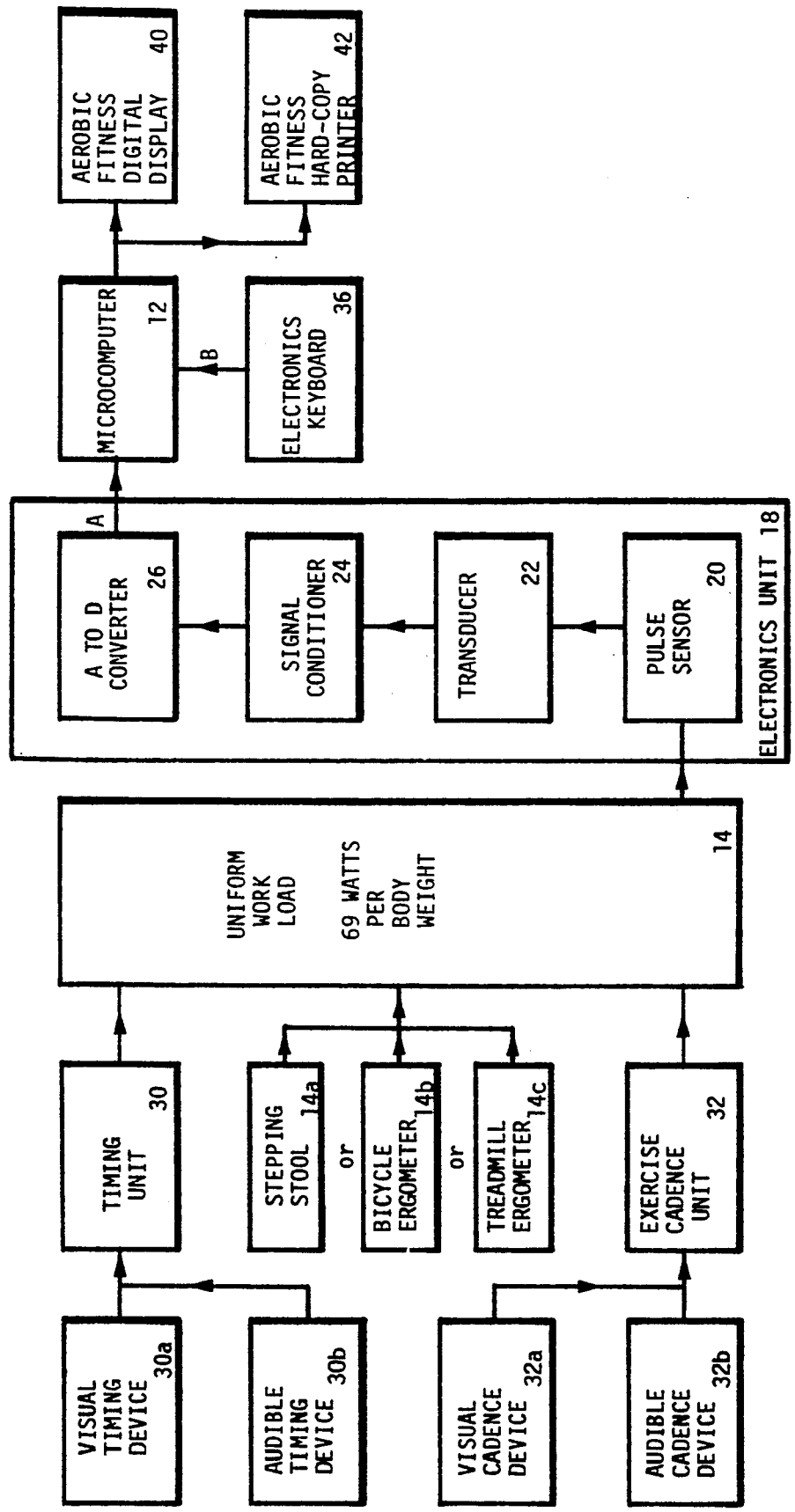
FIG. 1 is a block diagram of the universal fitness testing system.

The best mode for carrying out the universal fitness testing system 10 is presented in terms of a preferred embodiment that is primarily designed to allow individuals, in 30-seconds, to determine their aerobic fitness and to provide other fitness related information.

The preferred embodiment, as shown in FIGS. 1 through 5 is comprised of the following eight major elements: a data processor, that in the best mode consists of a microcomputer 12, a uniform work load 14 preferably consisting of a stepping stool 14a, an electronics unit 18, a timing unit 30, an exercise cadence unit 32, an electronics keyboard 36 and an aerobic fitness digital display 40 and a hard-copy printer 42.

The microcomputer 12, in the best mode, includes a microprocessor with its associated operational program, memory and control circuits. The microcomputer 12, which forms the operational basis for the universal fitness testing system 10 as shown in the block diagram of FIG. 1, receives two primary inputs: pulse-rate digital signals that correspond to the pulsations of an individual's cardiovascular system and a set of primary user-specific digital signals corresponding to the individual's age, body weight and sex. A set of secondary user-specific digital signals corresponding to altitude, temperature, humidity, altitude loss, altitude gain, load carried and terrain factor, when applicable, may also be processed by the microcomputer.

The pulse-rate signals, as shown in FIG. 1, result from a means of performing a 30-second timed exercise test that results in producing a uniform work load of 0.69 watts/kg of body weight. The timed test is performed by stepping up and down, nine times on a stepping stool 14a having a height of 23.5 centimeters (9.25 inches). Although the stepping stool is the preferred implement for performing the timed exercise test, other exercise implements such as a bicycle ergometer 14b or a treadmill 14c may also be used. When using one of the alternate exercise implements, it is set to produce the standard work load of 0.69 watts/kg of body weight in the 30-second period. The stepping stool is preferred for the following reasons:

- a stool is a simple and inexpensive apparatus compared with a bicycle or treadmill ergometers,
- the stepping exercise can be performed almost anywhere, while the use of a treadmill or bicycle ergometer is limited to specific locations,
- stepping is a natural activity whereas many people have no cycling experience and most people have no treadmill walking/running experience.

To assist the exercising individual in determining when to start and stop the timed exercise test, a timing unit 30, as shown in FIG. 1, may be employed that produces start and stop signals. The timing unit 30 may consist of a visual timing device 30a that produces visual start and stop signals and/or an audible timing unit 30b that produces audible start and stop signals.

To further assist the exercising individual, an exercise cadence unit 32, as also shown in FIG. 1, is provided that displays the required cadence during the performance period of the timed exercise test. The cadence unit 32 may consist of an analog or digital visual cadence device 32a and/or an audible cadence device 32b such as a metronome that produces audible cadence steps. The exercise cadence unit 32 may be designed to be started and stopped by the start and stop signals from the timing unit 30.

The uniform work load resulting from the timed exercise test is applied to a means consisting of an electronics unit 18 that quantifies the uniform work load into pulse-rate signals that correspond to the pulsations of the individual's cardiovascular system. The quantification commences by applying the heart-beat pulsations, resulting from the timed exercise test, to a sensor 20 that forms a component of the electronics unit 18 and that produces equivalent pulse-rate mechanical signals. In the best mode, the sensor is comprised of a finger pulse sensor that is small and easily adaptable to various mounting configurations.

From the sensor 20, the pulse-rate mechanical signals are applied to a transducer 22 that converts the signals to equivalent pulse-rate electrical signals. The output of the transducer 22 is applied through a signal conditioner 24 where the pulse-rate electrical signals are conditioned and converted into pulse-rate analog signals. These signals are then applied to an analog-to-digital converter 26 where the signals are converted to the pulse-rate digital signals that are applied to the microcomputer 12 where the signals are used in determining the individual's equilibrium heart rate.

The set of primary user-specific digital signals corresponding to the individuals age, body weight and sex and the set of secondary user-specific digital signals corresponding to altitude, temperature, humidity, altitude loss, altitude gain, load carried and terrain factor are derived from an electronic keyboard 36.

The keyboard is a manually inputted unit that converts the inputted user-specified data into corresponding digital signals and applies them to the microcomputer 12 as shown in FIG. 1. These signals are also used by the microcomputer in determining the individual's equilibrium heart rate.

Figure 2:
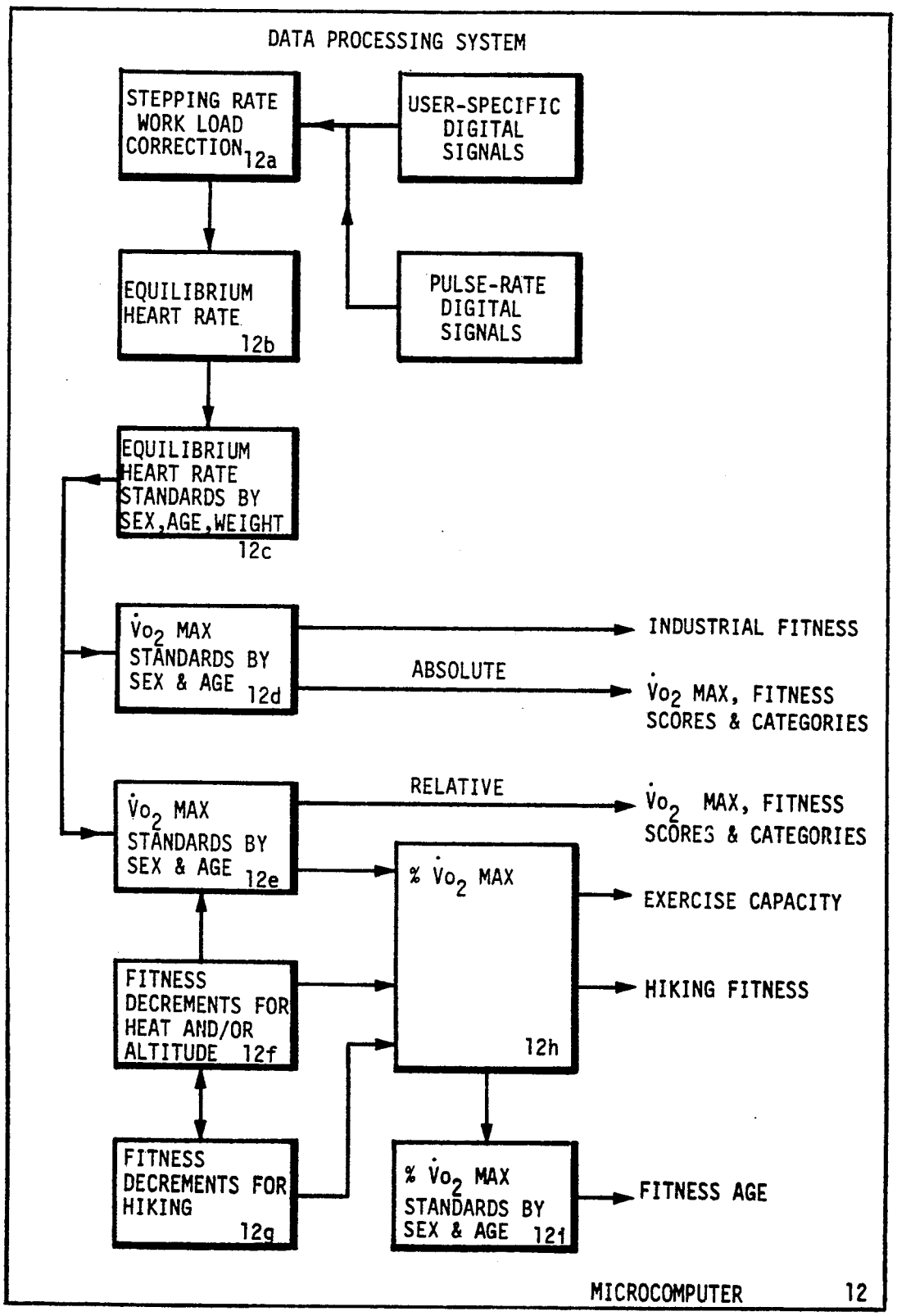
FIG. 2 is a block/flow diagram of the data processing system which includes its inputs and outputs.
Figure 4:
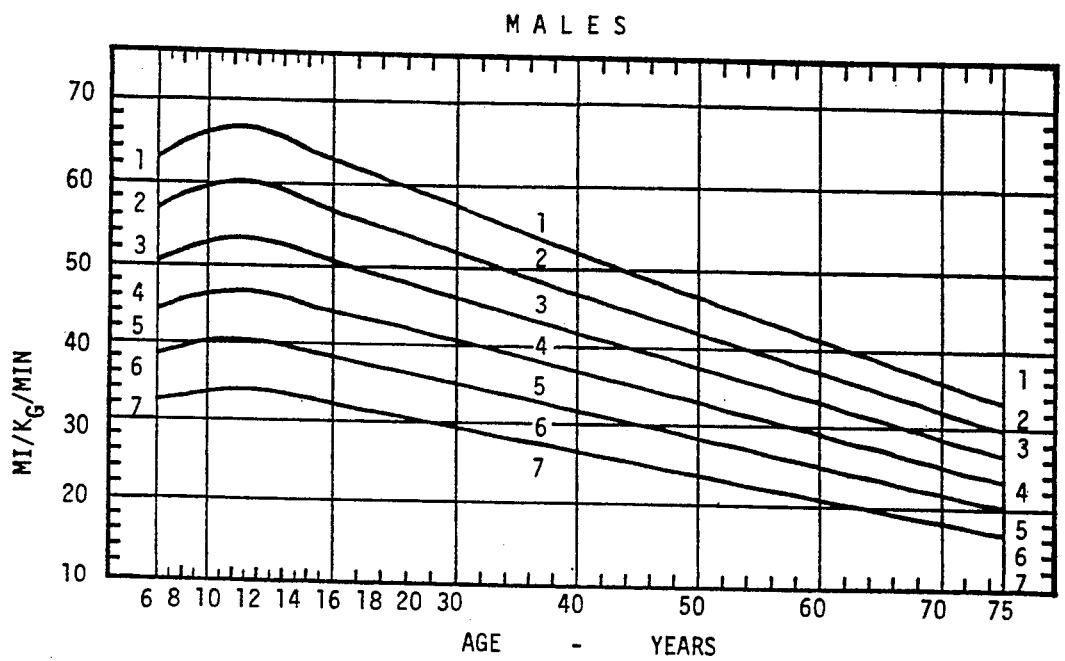
FIG. 4A, 4B is a diagram of the aerobic fitness ($V_{O_2}$ max) standards by sex and age for males.
Figure 4:
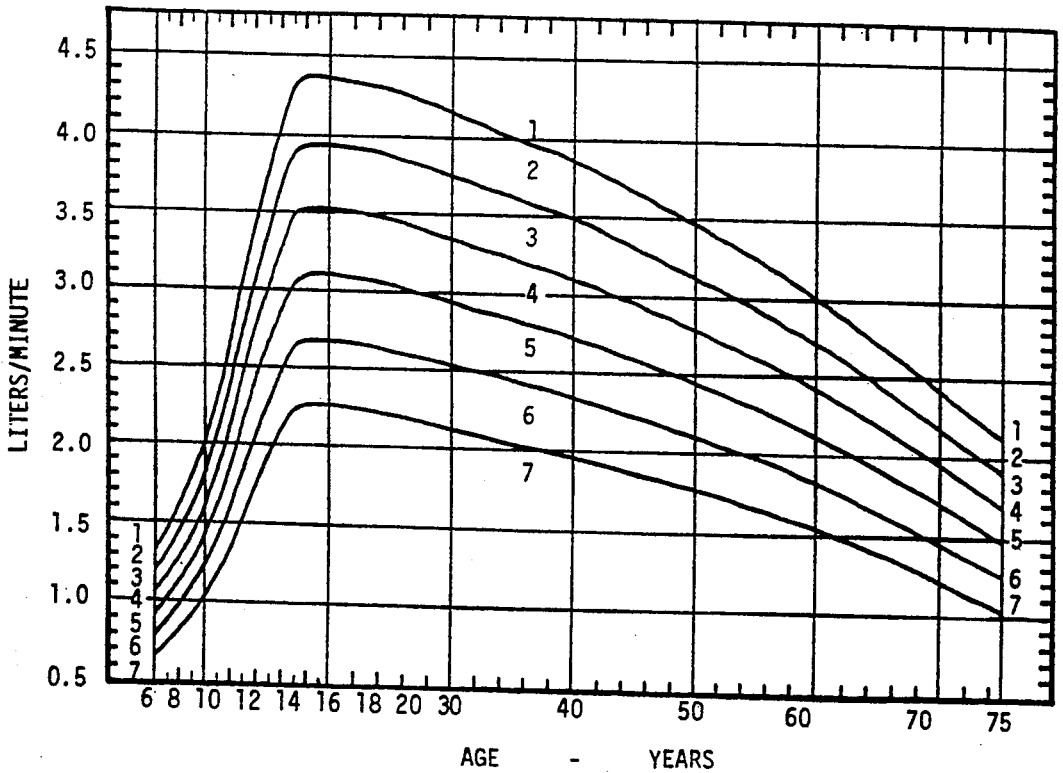

The operational functions of the data processor are shown in FIG. 2. The two inputs to the microcomputer are the pulse-rate digital signals and the user-specific digital signals. These signals are first applied to a stepping rate/work load correction circuit 12a that allows any discrepancy in the stepping rate of the timed exercise test to be corrected to the preferred uniform work load of 0.69 watts/body weight. This preferred work load is achieved by stepping on the stool 14a at a rate of 18 steps/minute (9 steps/30-seconds). Some individuals may step at other rates ranging from 12 to 30 steps/minute. These "other" rates may be detected by attaching a pressure sensor (not shown) to the stool 14a from where the sensed rate is applied directly to the correction circuit 12a; or, the rate may be entered by means of the keyboard 36 and subsequently applied to the correction circuit 12a.

Although, the system 10 can compensate for various stepping rates, the majority of individuals will not err when using the timing unit 30 in combination with the exercise cadence unit 32.

The output from the correction circuit 12a is the individual's equilibrium heart rate as designated by the block 12b. The equilibrium heart rate, corrected for stepping rate, is then further refined by a set of memory stored equilibrium heart rate standards. These standards correct for the individual's age, body weight and sex. Further correction is provided by a set of memory stored absolute 12d and relative 12e $V_{O_2}$ max standards categorized by sex and age as shown for females in FIGS. 3A, B and for males in FIGS. 4A, B.

From the standards 12d, 12e, as shown in FIG. 2, the following outputs, applicable to a specific individual, are produced:

(1) absolute $V_{O_2}$ max: given in liters/minute,
(2) relative $V_{O_2}$ max: given in ml/kg·min,
(3) fitness scores: ranging from 40 to 100 with an accuracy of ±1.0
where: 100 is excellent, 70 is average and 40 is very poor,
(4) fitness categories: categorized as excellent, very good, average, fair, poor and very poor; and
(5) industrial fitness: given in terms of the safe aerobic load that can be maintained in the performance of a work load without fatigue. Industrial fitness is ⅓ of absolute $V_{O_2}$ max.

The microcomputer 12 also includes a set of memory stored fitness decrements 12f, 12g that cover heat, altitude, hiking altitude gain or loss, type of hiking terrain and hiking load carried. The fitness decrements are applied to % $V_{O_2}$ max 12h. Percent $V_{O_2}$ max is the energy expenditure used during the 30-second timed, test and is expressed as a percentage of absolute $V_{O_2}$ max.

From the % $V_{O_2}$ max 12h, the following outputs, applicable to a specific individual are produced (1) exercise capacity: given in terms of the maximum rate of walking and/or running that can be maintained aerobically which also provides the maximum distance that can be covered in walking/running at the above speed, and
(2) hiking fitness: given in terms of the walking and/or running rate that can be maintained during a one-day hike. Hiking on a mild negative slope (downhill) results in an improved rate of walking or running while hiking on a steep negative slope results in a slower rate of progression.

The output from % $V_{O_2}$ max is also applied to a memory stored % $V_{O_2}$ max standards 12i categorized by sex and age. From the standards 12i, the specific individuals fitness age is determined. Fitness age is the chronological age that corresponds to a certain % $V_{O_2}$ max.

The keyboard inputs necessary to obtain altitude and/or heat related information include: altitude where the test is performed and altitude where the activity is to be performed. Also entered with respect to the site where the test is performed, and where the expected activity is to be performed are air temperature and one of three humidity levels: dry, average humidity or humid. The inputs for hiking fitness include: the weight of load carried, terrain factor where: 1=asphalt, 1.5=snow and 1.8=sand dunes, total distance of the hike, total sum of altitude gains (vertical distance), segment by segment of altitude loss or level walk in vertical distance per distance walked. The microcomputer 12 through its program can also process combinations of hiking fitness and heat and/or altitude factors. This additional fitness related information can be obtained by inputting the electronic keyboard 36 with entries made in meters, centigrade, kilograms or in feet, fahrenheit and pounds. A table, included as FIG. 5, lists the universal fitness testing system 10 inputs and outputs.

The outputs may be displayed via an analog or digital display 40 or a hard-copy printer 42 may be employed when permanent records are desired.

OPERATION

To use the universal fitness testing system 10, the following steps are performed:

(1) Enter the individual's age, body weight and sex and other desired inputs into the electronic keyboard 36,
(2) place a finger into the pulse sensor 20,
(3) perform the 30-second timed exercise test,
(4) obtain the aerobic fitness results from the digital display 40 or the hard-copy printer 42.

While the invention has been described in complete detail and pictorially shown in the accompanying drawings, it is not to be limited to such details, since many changes and modifications may be made to the invention without departing from the spirit and the scope thereof. Hence, it is described to cover any and all modifications and forms which may come within the language and scope of the claims.

We claim:

1. A universal fitness testing system for predicting aerobic fitness, said system comprising:
   a) means for obtaining pulse-rate data from a timed exercise test consisting of an individual stepping up and down on a stepping stool a specific number of times in a specific time period,
   b) pulse-rate digitizing means for producing pulse-rate digital signals from said pulse-rate data,
   c) means for producing an equilibrium heart rate from said pulse-rate digital signals,
   d) means for producing a set of primary user-specific digital signals corresponding to the individual's age, body weight and sex,
   e) data processing means for receiving and processing the pulse-rate digital signals and the user-specific digital signals with memory stored standards to produce predicted aerobic fitness data, and
   f) display means responsive to said aerobic fitness data for displaying the predicted aerobic fitness data.

2. The system as specified in claim 1 wherein said timed exercise test consists of stepping up and down said stepping stool nine times in a 30-second time period.

3. The system as specified in claim 1 wherein said pulse-rate digitizing means comprises:
   a) finger pulse sensing means for sensing cardiovascular system pulsations and outputting pulse-rate electrical signals resulting from the timed exercise test,
   b) signal conditioning means for conditioning and converting the pulse-rate electrical signals into analog pulse-rate signals, and
   c) analog-to-digital converting means for converting the analog pulse-rate signals into digital pulse-rate signals.

4. A universal fitness testing system for predicting aerobic fitness, said system comprising:
   a) means for obtaining pulse-rate data from a timed exercise test consisting of an individual stepping up and down on a stepping stool having a height of 23.5 centimeters (9.25 inches) nine times in a 30-second time period, b) pulse-rate digitizing means for producing pulse-rate digital signals from said pulse-rate data c) means for producing an equilibrium heart rate from said pulse-rate digital signals, d) means for producing a set of primary user-specific digital signals corresponding to the individual's age, body weight and sex, e) data processing means for receiving and processing the pulse-rate digital signals and the user-specific digital signals with memory stored standards to produce predicted aerobic fitness data, and f) display means responsive to said aerobic fitness data for displaying the predicted aerobic fitness data.

5. A universal fitness testing system for predicting aerobic fitness, said system comprising:

a) means for obtaining pulse-rate data from a timed exercise test consisting of an individual operating a bicycle ergometer for 30 seconds, b) pulse-rate digitizing means for producing pulse-rate digital signals from said pulse-rate data, c) means for producing an equilibrium heart rate from said pulse-rate digital signals, d) means for producing a set of primary user-specific digital signals corresponding to the individual's age, body weight and sex, e) data processing means for receiving and processing the pulse-rate digital signals and the user-specific digital signals with memory stored standards to produce predicted aerobic fitness data, and f) display means responsive to said aerobic fitness data for displaying the predicted aerobic fitness data.

6. A universal fitness testing system for predicting aerobic fitness, said system comprising:

a) means for obtaining pulse-rate data from a timed exercise test consisting of an individual operating a threadmill for 30 seconds, b) pulse-rate digitizing means or producing pulse-rate digital signals from said pulse-rate data, c) means for producing an equilibrium heart rate from said pulse-rate digital signals, d) means for producing a set of primary user-specific digital signals corresponding to the individual's age, body weight and sex, e) data processing means for receiving and processing the pulse-rate digital signals and the user-specific digital signals with memory stored standards to produce predicted aerobic fitness data, and f) display means responsive to said aerobic fitness data for displaying the predicted aerobic fitness data.

7. A universal fitness testing system for predicting aerobic fitness, said system comprising:

a) means for obtaining pulse-rate data from a timed exercise test consisting of an individual stepping up and down on a stepping stool a specific number of times in a specific time period, b) pulse-rate digitizing means for producing pulse-rate digital signals from said pulse-rate data, c) means for producing an equilibrium heart rate from said pulse-rate digital signals, d) means for producing a set of primary user-specific digital signals corresponding to the individual's age, body weight and sex, e) means for producing, a set of secondary user-specific digital signals corresponding to altitude, temperature, humidity, altitude loss, altitude gain, load carried and terrain factor, f) data processing means for receiving and processing the pulse-rate digital signals and the user-specific digital signals with memory stored standards to produce predicted aerobic fitness data, and g) display means responsive to said aerobic fitness data for displaying the predicted aerobic fitness data.

8. A universal fitness testing system for predicting aerobic fitness, said system comprising:

a) means for obtaining pulse-rate data from a timed exercise test consisting of an individual stepping up and down on a stepping stool having a height of 23.5 centimeters (9.25 inches) nine times in a 30-second time period, b) pulse-rate digitizing means for producing pulse-rate digital signals from said pulse-rate data, c) means for producing an equilibrium heart rate from said pulse-rate digital signals, d) means for producing a set of primary user-specific digital signals corresponding to the individual's age, body weight and sex, e) data processing means for receiving and processing the pulse-rate digital signals and the user-specific digital signals with memory stored standards to produce predicted aerobic fitness data, where said data processing means further comprises:

(1) first memory compensation means for storing a set of equilibrium heart rate standards and in compensating for an individual's heart rate based on age, body weight and sex, (2) second memory compensation means for storing a set of absolute and relative $Vo_2$ max standards categorized by sex and age that for compensating the individual's equilibrium heart rate and for producing the following outputs:

(a) absolute $Vo_2$ max: in liters/minute, (b) relative $Vo_2$ max: in ml/kg min, (c) fitness scores: ranging from 40 to 100 where: 100 is excellent, 70 is average and 40 is very poor, (d) fitness categories: categorized as excellent, very good, good, average, fair, poor and very poor, (e) industrial fitness: in terms of the aerobic load that can be maintained in the performance of a work load without fatigue and, f) display means responsive to said aerobic fitness data for displaying the said outputs.

9. A universal fitness testing system for predicting aerobic fitness, said system comprising:

a) means for obtaining pulse-rate data from a timed exercise test consisting of an individual stepping up and down on a stepping stool a specific number of times in a specific time period, b) pulse-rate digitizing means for producing pulse-rate digital signals from said pulse-rate data, c) means for producing an equilibrium heart rate from said pulse-rate digital signals, d) means for producing a set of primary user-specific digital signals corresponding to the individual's age, body weight and sex, e) data processing means for receiving and processing the pulse-rate digital signals and the user-specific digital signals with memory stored standards to produce predicted aerobic fitness data, where said data processing means further comprises:

(1) first memory compensating means for storing a set of equilibrium heart rate standards and for compensation for individual's heart rate based on age, body weight and sex, (2) second memory compensation means for storing a set of memory stored absolute and relative $Vo_2$ max standards categorized by sex and age that for compensating the individual's equilibrium heart rate and for producing for a specific individual the following outputs:
  (a) absolute $Vo_2$ max: in liters/minute,
  (b) relative $Vo_2$ max: in ml/kg min,
  (c) fitness scores: ranging from 40 to 100 where: 100 is excellent, 70 is average and 40 is very poor,
  (d) fitness categories: categorized as excellent, very good, good, average, fair, poor and very poor,
  (e) industrial fitness: in terms of the aerobic load that can be maintained in the performance of a work load without fatigue and, (3) third memory compensation means for storing a set of fitness decrements that cover heat, altitude, hiking altitude gain or loss, type of hiking terrain and hiking load carried; where these decrements are applied to % $Vo_2$ max,
  (a) exercise capacity: in terms of the maximum rate of walking and/or running that can be maintained aerobically, and
  (b) hiking fitness: in terms of the walking and/or running rate that can be maintained during a one-day hike, and (4) a set of memory stored % $Vo_2$ max standards by sex and age where these standards are used to correct % $Vo_2$ max to determine an individual's fitness age, and f) display means responsive to said aerobic fitness data for displaying said outputs.

* * * * *